United States Patent
Heumann et al.

(10) Patent No.: US 12,239,795 B2
(45) Date of Patent: Mar. 4, 2025

(54) THORACIC CATHETER

(71) Applicant: Universitaetsklinikum Hamburg-Eppendorf, Hamburg (DE)

(72) Inventors: Asmus Heumann, Hamburg (DE); Jakob Izbicki, Hamburg (DE)

(73) Assignee: Universitaetsklinikum Hamburg-Eppendorf, Hamburg (DE)

( * ) Notice: Subject to any disclaimer, the term of this patent is extended or adjusted under 35 U.S.C. 154(b) by 685 days.

(21) Appl. No.: 17/422,498

(22) PCT Filed: Jan. 20, 2020

(86) PCT No.: PCT/EP2020/051215
§ 371 (c)(1),
(2) Date: Jul. 13, 2021

(87) PCT Pub. No.: WO2020/152071
PCT Pub. Date: Jul. 30, 2020

(65) Prior Publication Data
US 2022/0062583 A1    Mar. 3, 2022

(30) Foreign Application Priority Data
Jan. 21, 2019 (EP) .................................... 19152858

(51) Int. Cl.
*A61M 25/00* (2006.01)

(52) U.S. Cl.
CPC . *A61M 25/0043* (2013.01); *A61M 2025/0057* (2013.01); *A61M 2205/02* (2013.01)

(58) Field of Classification Search
CPC ...................... A61M 25/0043; A61M 2205/02
See application file for complete search history.

(56) References Cited

U.S. PATENT DOCUMENTS 4,263,236 A * 4/1981 Briggs .................... B29C 65/78
                                                          264/491
5,810,786 A    9/1998 Jackson et al.
(Continued)

FOREIGN PATENT DOCUMENTS

CN        203001642 U      6/2013
CN        204972656    *   1/2016 ............ A61M 25/10
(Continued)

OTHER PUBLICATIONS

International Search Report issued on Mar. 26, 2020, in International Application No. PCT/EP2020/051215.
(Continued)

*Primary Examiner* — Robert J Utama
*Assistant Examiner* — John A Doubrava
(74) *Attorney, Agent, or Firm* — Patent Central LLC; Stephan A. Pendorf

(57) ABSTRACT

A thoracic catheter for a comparatively simple and reliable control and relief of pain associated with thoracatomy. The thoracic catheter (1) has a distal end (2), a proximal end (3) and an intercostal region (4) in between. The thoracic catheter (1) is covered on its outer surface (6) in the intercostal region (4) with a capillary active layer (5), which is fluidically connectable to a distal source (7) of an anesthetic agent, and which, when arranged in the body of a patient, is capable of releasing the anesthetic agent into the intercostal space (21).

13 Claims, 3 Drawing Sheets

(56) References Cited

U.S. PATENT DOCUMENTS

Figure 1:
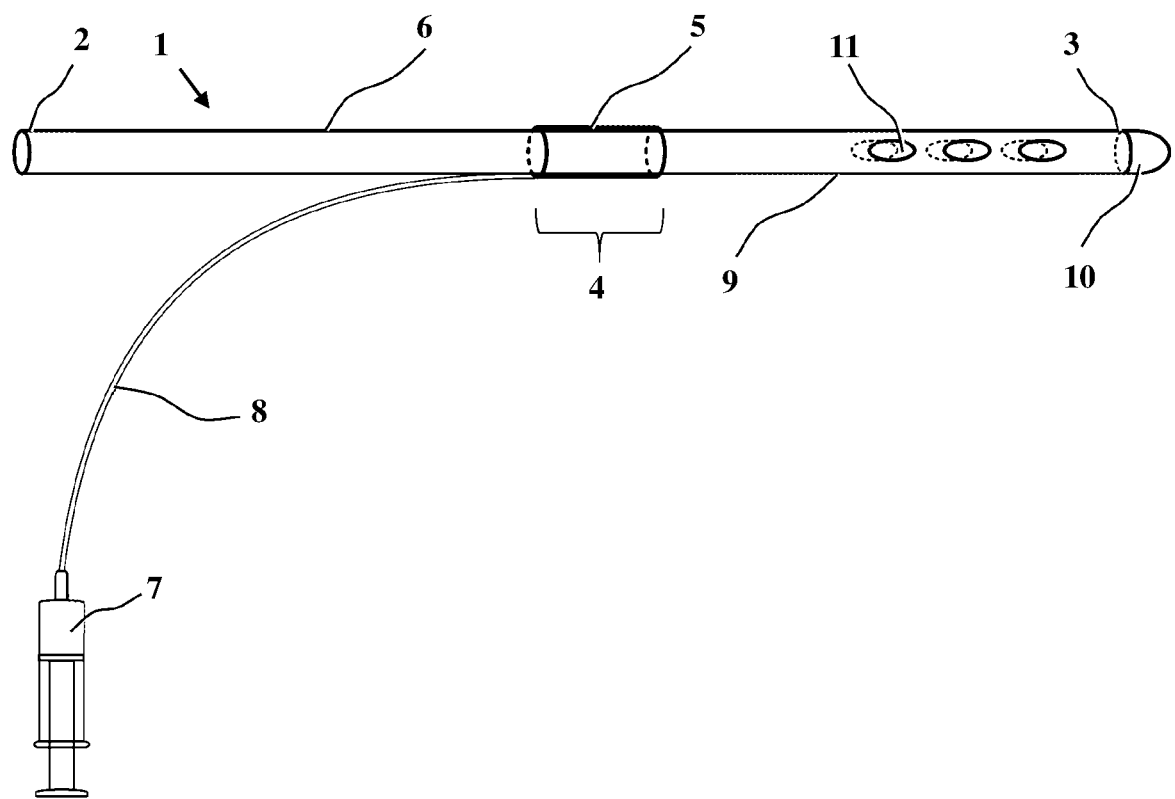

| | | | |
|---|---|---|---|
| 6,461,644 B1 | 10/2002 | Jackson et al. | |
| 2006/0088565 A1* | 4/2006 | Kohnert | A61L 27/12 424/602 |
| 2010/0179513 A1* | 7/2010 | Hebeler, Jr. | A61M 27/00 604/537 |
| 2011/0137267 A1* | 6/2011 | Phillips | A61M 25/0068 604/290 |
| 2013/0184742 A1* | 7/2013 | Ganesan | A61M 25/0029 606/200 |

FOREIGN PATENT DOCUMENTS

| | | | |
|---|---|---|---|
| CN | 204972656 U * | 1/2016 | |
| WO | 9839042 A1 | 9/1998 | |
| WO | 2004043518 A2 | 5/2004 | |
| WO | 2005062886 A2 | 7/2005 | |
| WO | 2018144898 A1 | 8/2018 | |

OTHER PUBLICATIONS

May, Gabby, et al.: "The use of intrapleural anaesthetic to reduce the pain of chest drain insertion", [published correction appears in Emerg Med J. Sep. 2007;24(9):685; Dosage error in article text]; Emerg Med J. 2007; 24 (4):300-301; doi:10.1136/emj.2007.047878; see https://www.ncbi.nlm.nih.gov/pmc/articles/PMC2658245/.

Kang, Hyun, et al.: "Application of Lidocaine Jelly on Chest Tubes to Reduce Pain Caused by Drainage Catheter after Coronary Artery Bypass Surgery"; J Korean Med Sci.; Oct. 2014; 29; pp. 1398-1403; http://dx.doi:10.3346/jkms.2014.29.10.1398.

* cited by examiner

THORACIC CATHETER

The invention relates to a thoracic catheter.

Postoperative pain is one of the reasons leading to discomfort and prolonged convalescence times in patients. Thoracotomy, a frequent surgical procedure for gaining access into the pleural space of the chest, involves thoracic drainage systems causing high levels of pain in patients due to its positioning in the intercostal space. The treatment of patients with painkillers, especially using a peridural catheter (PDC), numbing the nerves near the spine significantly improves recovery. However, a PDC can not be applied to all patients, e.g. in case of an emergency procedure or in case of coagulation disorders. In addition, systemic administration of painkillers may lead to an increased burden on the organism, so that a possibility to numb the pain-causing region directly in the form of local anesthetics is clearly to be preferred (see e.g. G. May, 2007, The use of intrapleural anaesthetic to reduce the pain of chest drain insertion, Emerg. Med. J. 24(4):300-301. doi:10.1136/emj.2007.047878). Also in case of a spontaneous pneumothorax or a pleural effusion drainage a local anesthesia is required.

U.S. Pat. Nos. 5,810,786 B1 and 6,461,644 B1 describe intubation devices, such as chest drainage tubes, that have a local anesthetizing effect. A local anesthetic is dissolved in a thermoplastic resin, for example polyvinyl chloride, forming the tube wall or outer layer of the tube. While in place within the body passage the anesthetic diffuses to the surface of the body tissue touched by the tube.

WO 2005/062886 A2 describes a catheter with an exterior layer of a pain reliever.

Kang et al. 2014 describe the application of a jelly of the local anesthetic Lidocaine to chest tubes for pain reduction (Kang H, Chung Y S, Choe J W, Woo Y C, Kim S W, Park S J, Hong J, 2014, Application of Lidocaine Jelly on Chest Tubes to Reduce Pain Caused by Drainage Catheter after Coronary Artery Bypass Surgery, Journal of Korean Medical Science, 29(10), 1398-1403. http://doi.org/10.3346/jkms.2014.29.10.1398).

CN 203001642 U relates to a branched catheter having three branches disposed on a main catheter, each branch having a plurality of micropores through which an analgesic can be introduced into the body in order to simultaneously anesthetize severeal intercostal nerves during thoracotomy.

There is still a need for a simple and reliable pain control in thoracotomy.

It is thus an object of the invention to provide a means for a comparatively simple and reliable control and relief of pain associated with thoracatomy.

In order to solve the object, the invention provides a thoracic catheter having a distal end, a proximal end and an intercostal region in between, wherein the thoracic catheter is covered on its outer surface in the intercostal region with a capillary active layer, which is fluidically connectable to a distal source of an anesthetic agent, and which, when arranged in the body of a patient, is capable of releasing the anesthetic agent into the intercostal space.

The term "thoracic catheter" relates to usually flexible tube-like, i.e. generally hollow-cylindrically formed medical instruments used to remove air, blood or other body fluids from the intrathoracic space, for example the pleural cavities. Thoracic catheters are frequently made of a suitable plastic material, for example polyvinyl chloride or silicone. The terms "chest tube", "chest drain", "intercostal drain", "intercostal catheter" or "Mi.lau drain" are also used synonymously.

The term "intercostal space" (ICS, lat. spatium intercostale) relates to the space between two ribs.

The terms "pleural cavity" or "pleural space" (lat. cavitas pleuralis or cavum pleurae) relate to the space between the two pleurae (visceral and parietal) of the lung, which is normally comparatively small and contains pleural fluid. The outer pleura (parietal pleura, lat. pleura parietalis) is attached to the chest wall while the inner pleura (visceral pleura, lat. pleura visceralis) covers the lungs. The parietal pleurae are highly sensitive to pain (see, for example, Charalampidis C. et al, 2015, Pleura space anatomy, J Thorac Dis. 7(Suppl 1): 27-S32, doi: 10.3978/j.issn.2072-1439.2015.01.48).

The term "thoracotomy" relates to a surgical procedure to gain access into the pleural space of the chest.

The term "intercostal region" in relation to the thoracic catheter of the invention relates to the region of the thoracic catheter, which, when in place, i.e. inserted in the chest of a patient, is arranged in the intercostal space.

The term "distal" as used herein has the usual meaning and relates to a position or direction away or more remote from the centre of the body, in particular the insertion point of the thoracic catheter in the chest.

The term "proximal" as used herein has the usual meaning and relates to a position or direction nearer to the centre of the body, in particular the insertion point of the thoracic catheter in the chest.

The term "capillary active layer" as used herein relates to a layer having a capillary activity. Having "capillary activity" means that the material has the property to distribute a liquid by means of capillary forces within itself. The term "capillary net" may also be synonymously be used herein in relation to capillary active layer.

An "anesthetic agent" as used herein relates to any compound or composition inducing insensitivity to pain or acting to relief pain, preferably locally. The terms "analgesic" or "painkiller" may also be used synonymously.

The expression according to which the thoracic catheter "is covered on its outer surface in the intercostal region with a capillary active layer" means that at least a partial areas of the outer surface of the thoracic catheter in the intercostal region has a capillary active layer. The expression includes that the capillary active layer may be present over the whole outer surface in the intercostal region, i.e. encases the catheter in that region.

The invention provides a means for efficiently avoiding or relieving pain associated with thoracotomy. The thoracic catheter of the invention features a layer of capillary active material in a region of the thoracic catheter, which will come to lie in the intercostal space when inserted in the chest of a patient. The layer is fluidically connected, e.g. via a tube, to a source of an anesthetic agent, such that the anesthetic agent can be fed to the capillary active material. The anesthetic agent is distributed by means of capillary forces in the capillary active layer and is released from the capillary active layer into the environment, i.e. into the intercostal space in order to numb the nerves there.

The amount of anesthetic agent released into the environment can easily be controlled. The active agent can, for example, be passively fed to the layer of capillary active material and released into the intercostal space, e.g. via capillary action and diffusion, and/or actively via a syringe, pump or other dosage device.

The anesthetic agent may be a local anesthetic agent, e.g. procaine, lidocaine or bupivacaine, which lasts for up to 12 hours. Preferably, the "anesthetic agent" is in liquid form.

The capillary active layer may comprise or consist of a fabric made of a biocompatible material, e.g. silicone. The capillary active layer may also comprise or consist of a spongy or net-like structure made of a suitable plastic material, e.g. silicone, of e.g. silicone fibers or filaments spirally wound around the respective surface area of the thoracic catheter, of hollow fibers or filaments having pores through which the anesthetic agent can be released, or combinations thereof. Fibers or filaments, e.g. of silicone, may be connected to each other in the transverse direction, such that a mat- or sleve-like structure is formed with projecting ribs and grooves inbetween, the grooves and ribs running spirally around the peripheral surface of the thoracic catheter. The capillary active grooves spiraling around the catheter distribute an anesthetic agent in a particularly efficient manner.

In a preferred embodiment of the invention, the thoracic catheter comprises a tube, preferably a capillary tube, i.e. a tube of a small inner diameter, which is fluidically connected to the capillary active layer and is fluidically connectable to the distal source of an anesthetic agent.

The tube is directly or indirectly connected to the source of the anesthetic agent. The tube may be of any suitable biocompatible material, and can, for example, be a metal capillary or a silicone tube. The tube and the capillary active layer may both be made of silicone. In this case, the tube may be formed in one piece with or fused to the capillary active layer.

The thoracic catheter may be of any suitable biocompatible material, preferably of a flexible biocompatible plastic material, preferably of silicone.

It is preferred that the capillary active layer does not essentially enlarge the cross-section of the catheter, such that the incision for introducing the catheter into the body can be kept small and the intercostal muscles are not unnecessarily stretched. The capillary active layer is thus preferably as thin as possible. Alternatively or additionally, however, the capillary active layer can be arranged in a recess of the wall of the thoracic catheter. In this manner, an enlargement of the cross-section of the catheter can be avoided and the capillary active layer can be thicker. It is preferred that in an embodiment where the capillary active layer is arranged in a recess of the wall of the thoracic catheter, the outer surface of the capillary active layer is flush with the surface of the adjacent parts of the thoracic catheter. is flush with the surface of the adjacent parts of the thoracic catheter.

The invention also relates to a thoracotomy kit comprising a thoracic catheter of the invention. The kit may, for example, comprise a) a preferably generally tube-like thoracic catheter, as described above, having a distal end, a proximal end and an intercostal region in between, wherein the thoracic catheter is covered on its outer surface in the intercostal region with a capillary active layer, and b) a tube, preferably a capillary tube, which is fluidically connectable to the capillary active layer.

In a preferred embodiment of the thoracotomy kit of the invention the tube is fluidically connected to the capillary active layer. In this embodiment, the tube, which preferably is a capillary tube, is already fluidically connected to the capillary active layer. The tube may be formed in one piece with or fused to the capillary active layer, e.g. in case both are of silicone or another plastic material.

In a preferred embodiment the thoracotomy kit additionally comprises a container containing an anesthetic agent, preferably in liquid form. The container may be a bottle or a syringe containing the anesthetic agent. A syringe for application of an anesthetic agent may be prefilled with "single shot" anesthetic agent. In case of using long lasting anesthetic agents like e.g. bupivacaine an application two- to three times per day should be effective.

In a further preferred embodiment the thoracotomy kit comprises a syringe fluidically connectable to the tube. The syringe may be empty or already filled with the anesthetic agent.

As an alternative, the capillary tube may be equipped with a suitable connector in order to be connectable to a pump providing the anesthetic agent continuously. The pump can be controlled by the medical staff as well as by the patient.

Preferably, all components of the kit are presterilizied and sterile packed.

In the following, the invention is further described for illustration purposes only by way of the attached figures and examples.

FIG. 1. Schematic view of an embodiment of a thoracic catheter of the invention.

Figure 2:
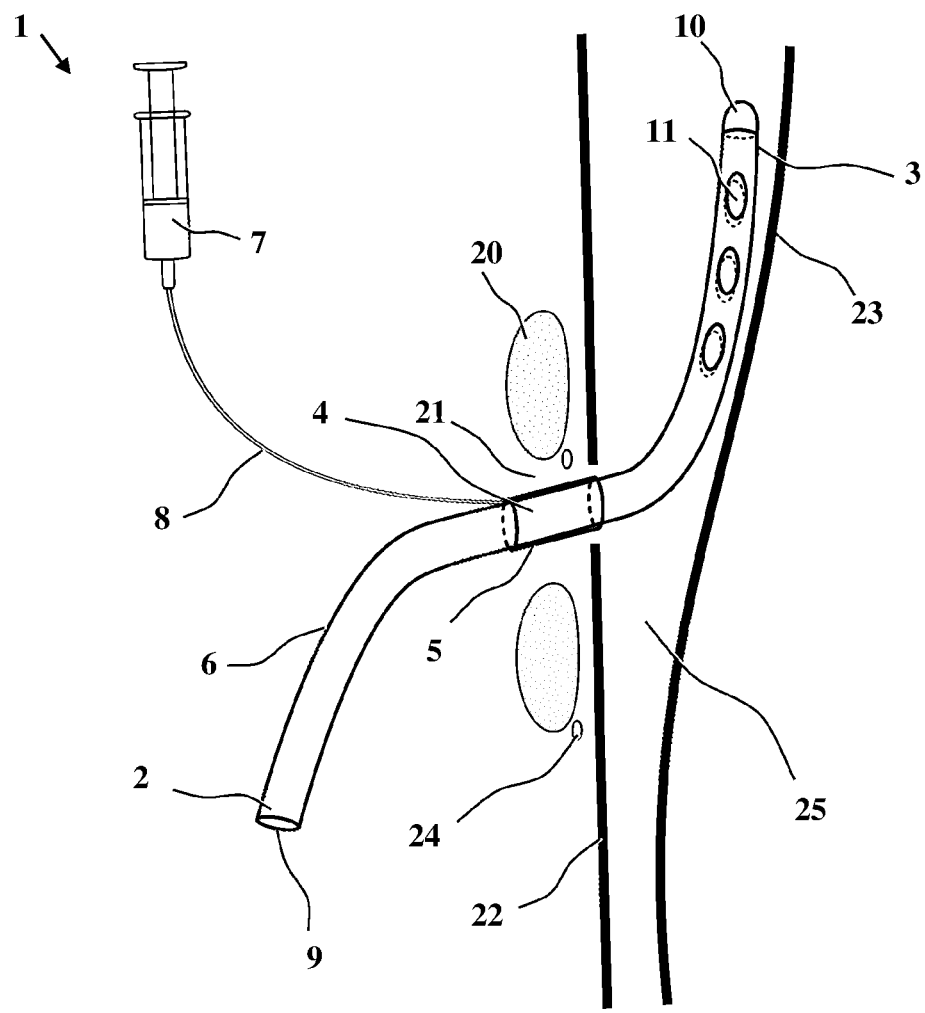

FIG. 2. Schematic view of an embodiment of a thoracic catheter of the invention in place, i.e. inserted in the chest of a patient.

Figure 3:
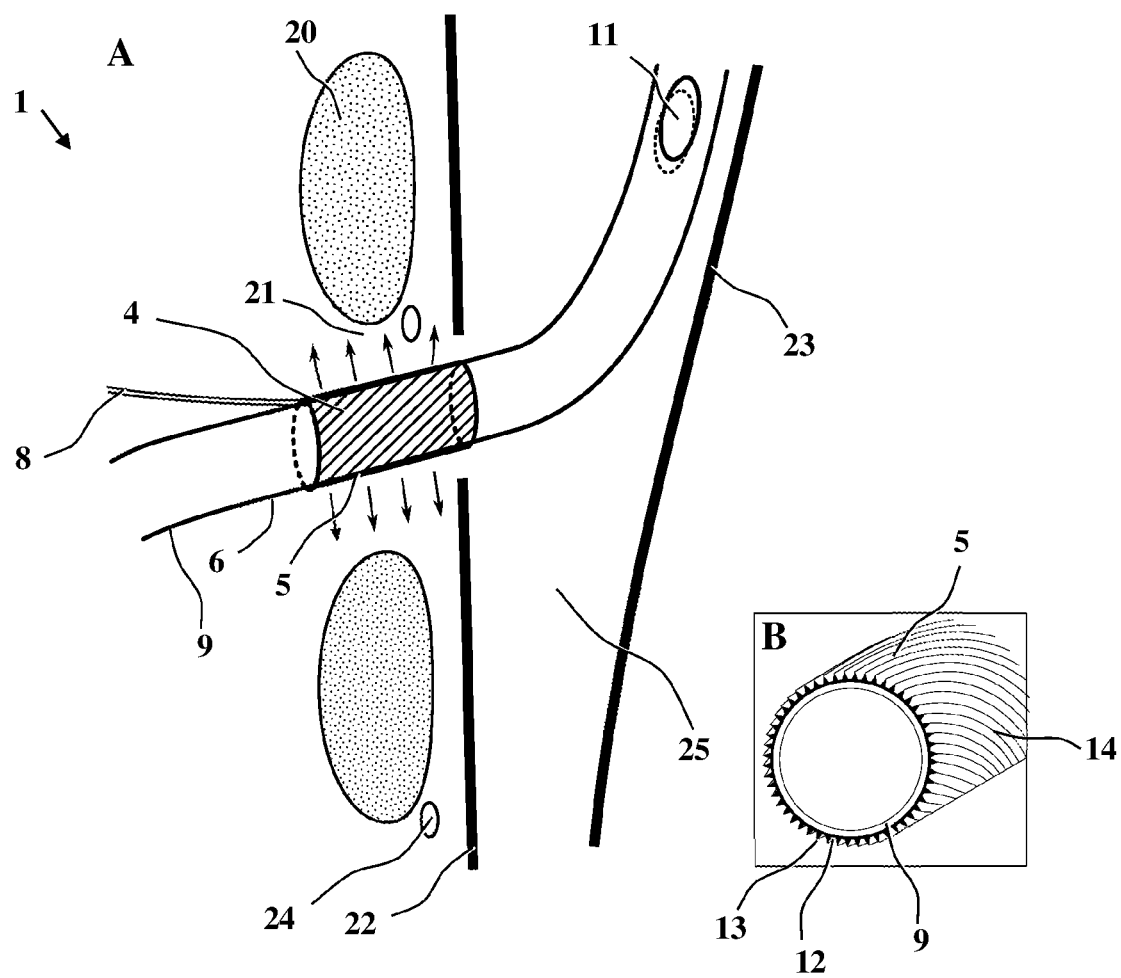

FIG. 3. A. Enlarged view of a part of FIG. 2. B. Cross-sectional view of capillary layer.

FIG. 1 shows an embodiment of a thoracic catheter 1 of the invention. The hollow-cylindrical thoracic catheter 1 has a distal end 2 and a proximal end 3. The thoracic catheter 1 will be inserted in the chest of a patient with the proximal end 3, while the distal end 2 remains outside the body. In this embodiment, a capillary active layer 5 is arranged on the surface 6 of the thoracic catheter 1 in its intercostal region 4, i.e. the region that will come to lie in the intercostal space 21 (see also FIG. 2). The capillary active layer 5 could also be arranged in a recess in the wall 9 of the thoracic catheter 1. The proximal end 3 has an atraumatic tip 10, i.e. a tapered tip, in order to facilitate the introduction of the thoracic catheter 1 into the body. Near the proximal end 3 the thoracic catheter 1 has six openings 11 in its wall 9 for the discharge or suction of air and/or body fluid.

The capillary active layer 5 is connected via a tube 8, here a capillary tube, with an external source 7 (here contained in a syringe) of an anesthetic agent. The anesthetic agent is preferably provided in the form of a fluid which can passively, e.g. via diffusion, or actively be fed to the capillary active layer 5, and to the intercostal space 21. The anesthetic agent is preferably distributed throughout the capillary active layer 5 by capillary forces and released from the capillary active layer 5 into the intercostal space 21.

In the sectional view of FIG. 2 the thoracic catheter 1 of FIG. 1 is shown in place, i.e. introduced into the pleural space 25 between the parietal pleura 22 and the visceral pleura 23 through the intercostal space 21 between two ribs 20 of a patient and the parietal pleura 22. The capillary active layer 5 is arranged in the intercostal space 21 and connected via a capillary tube 8 with the source 7 of an anesthetic agent, here contained in a syringe. The anesthetic agent can be fed to the capillary active layer 5 via the capillary tube 8 and to the intercostal nerves 24 in the intercostal space 21 in order to relief the pain induced by the surgical intervention.

FIG. 3 shows an enlarged view of a part of FIG. 2 showing the thoracic catheter 1 having a capillary active layer 5 with silicone fibers or filaments 14 running spirally around the peripheral surface of the thoracic catheter 1. As can be seen from FIG. 3B, the fibers or filaments 14 are connected at their bases with each other in the transverse direction and project from the mat- or sleeve-like structure thus formed, forming ribs 13 with grooves 12 in between, the grooves 12 and ribs 13 running spirally around the peripheral surface of the thoracic catheter 1. The capillary active grooves 12 spiraling around the thoracic catheter 1 distribute an anesthetic agent delivered to the grooves 12 via the tube 8. Since the grooves 12 run diagonally to the longitudinal axis of the catheter, a larger area of the intercostal space can be supplied with an anesthetic.

The invention claimed is:

1. A thoracic catheter (1) having a distal end (2), a proximal end (3) and an intercostal region (4) in between, wherein the thoracic catheter (1) includes a tube-like structure having an outer wall (9), the outer wall (9) having a recess in the intercostal region (4), wherein a capillary active layer (5) comprising fibers or filaments (14) running spirally around the thoracic catheter (1) is arranged in the recess of the outer wall (9), the capillary active layer (5) fluidically connectable to a distal source (7) of an anesthetic agent, and which capillary active layer (5), when arranged in the body of a patient, is capable of releasing the anesthetic agent into the intercostal space (21).

2. The thoracic catheter (1) according to claim 1, wherein the thoracic catheter (1) further comprises a tube (8), which is fluidically connected to the capillary active layer (5) and is fluidically connectable to the distal source (7) of an anesthetic agent.

3. The thoracic catheter (1) according to claim 1, wherein the thoracic catheter (1) is made of a flexible biocompatible plastic material.

4. The thoracic catheter (1) according to claim 1, wherein the outer surface of the capillary active layer (5) is flush with the surface of the adjacent non-recessed outer wall (9) of the thoracic catheter (1).

5. The thoracic catheter (1) according to claim 1, wherein the fibers or filaments (14) are interconnected in the transverse direction forming ribs (13) and grooves (12), the ribs (13) and grooves (12) running spirally around the thoracic catheter (1).

6. The thoracic catheter (1) according to claim 1, wherein the thoracic catheter (1) further comprises a capillary tube which is fluidically connected to the capillary active layer (5) and is fluidically connectable to the distal source (7) of an anesthetic agent.

7. The thoracic catheter (1) according to claim 3, wherein the thoracic catheter (1) is made of silicone.

8. A thoracotomy kit, comprising a thoracic catheter (1) of claim 1.

9. The thoracotomy kit according to claim 8, comprising
a) the thoracic catheter (1) of claim 1, and
b) a tube (8) which is fluidically connectable to the capillary active layer (5).

10. The thoracotomy kit according to claim 8, additionally comprising a container containing an anesthetic agent.

11. The thoracotomy kit according to claim 8, comprising a syringe fluidically connectable to the tube (8).

12. The thoracotomy kit according to claim 8, comprising
a) the thoracic catheter (1) of claim 1, and
b) a capillary tube which is fluidically connectable to the capillary active layer (5).

13. The thoracotomy kit according to claim 9, wherein the tube (8) is fluidically connected to the capillary active layer (5).

* * * * *